United States Patent
Cawood et al.

[11] 4,025,776
[45] May 24, 1977

[54] DOOR CLOSURE FOR FIBER OPTIC LIGHT SOURCE

[75] Inventors: Charles David Cawood, Houston, Tex.; Donald J. Mosior, Mundelein, Ill.

[73] Assignee: American Hospital Supply Corporation, Evanston, Ill.

[22] Filed: Sept. 18, 1975

[21] Appl. No.: 614,499

[52] U.S. Cl. .......................... 240/1 LP; 32/DIG. 7; 128/6; 128/11; 128/398; 350/96 B
[51] Int. Cl.² .............................................. G02B 5/14
[58] Field of Search ............... 240/1 EI, 1 LP, 2 E, 240/2 MT, 2.18, 6.46; 350/96 R, 96 B, 96 C, 96 T; 128/6, 11, 13, 16, 398; 32/DIG. 7, 69

[56] References Cited
UNITED STATES PATENTS

| | | | |
|---|---|---|---|
| 3,265,881 | 8/1966 | Hovnanian et al. | 240/1 EL X |
| 3,382,353 | 5/1968 | Wappler | 240/1 LP |
| 3,638,013 | 1/1972 | Keller | 240/1 LP X |
| 3,643,622 | 2/1972 | Cryer | 240/1 EL X |
| 3,683,167 | 8/1972 | Rishton | 240/1 E L |
| 3,758,951 | 9/1973 | Scrivo et al. | 240/1 LP X |
| 3,775,606 | 11/1973 | Bazell et al. | 240/1 LP X |
| 3,831,017 | 8/1974 | Auer | 240/1 LP X |

*Primary Examiner*—Richard A. Wintercorn

[57] ABSTRACT

A fiber optic light source is provided with a door for closing the source of light from the receptacle for a fiber optic light bundle. The light source is mounted within a frame having an opening through which light can pass, and a receptacle for the fiber optic light bundle is mounted on the frame and includes at least one opening which is alignable with the opening in the frame. The door is also provided with an opening and is movable between a first position in which the door opening is aligned with the opening in the frame and a second position in which the door opening is not aligned with the opening in the frame and light is blocked from the receptacle.

7 Claims, 4 Drawing Figures

U.S. Patent  May 24, 1977  4,025,776
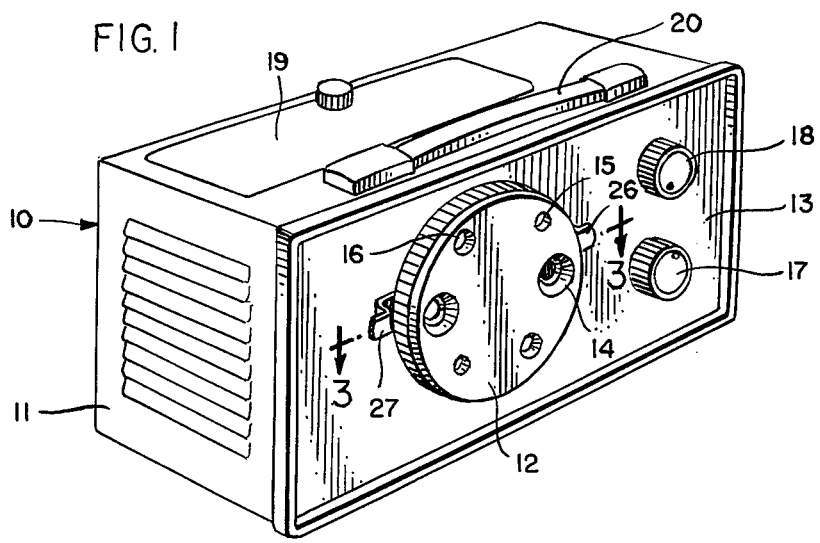
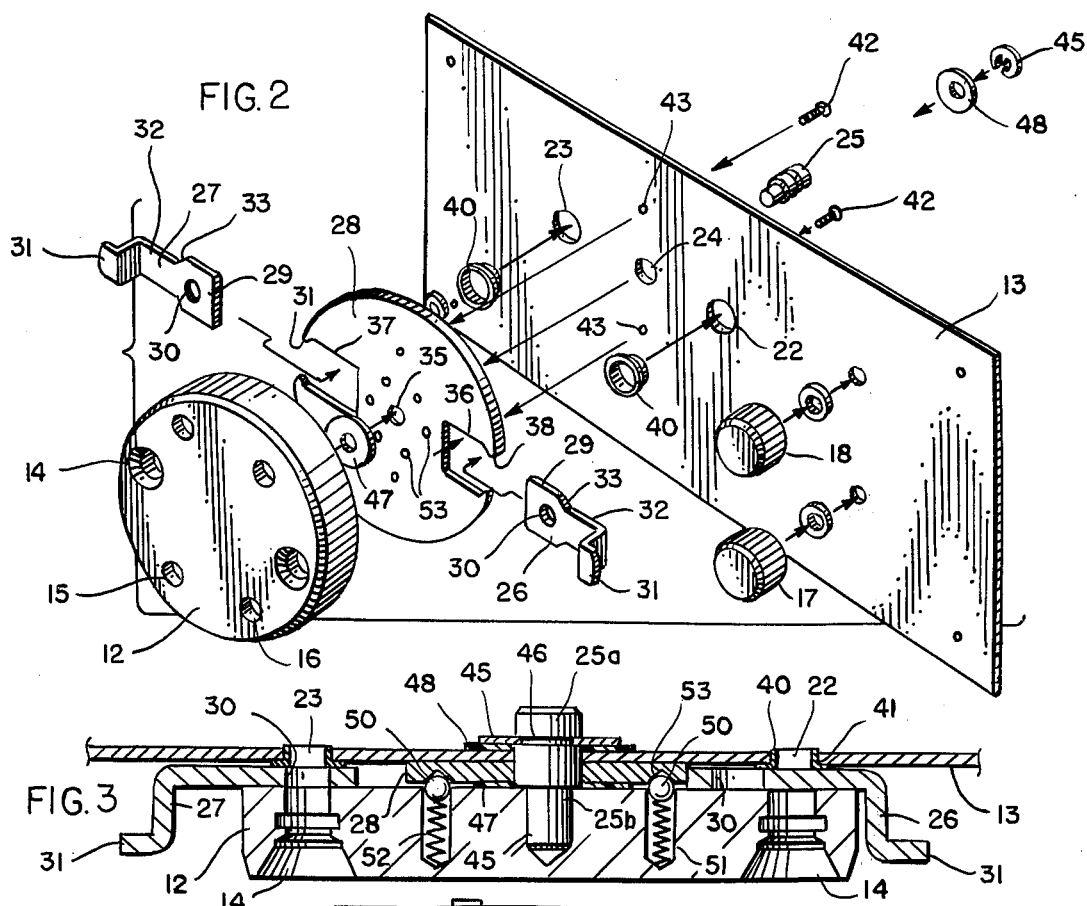
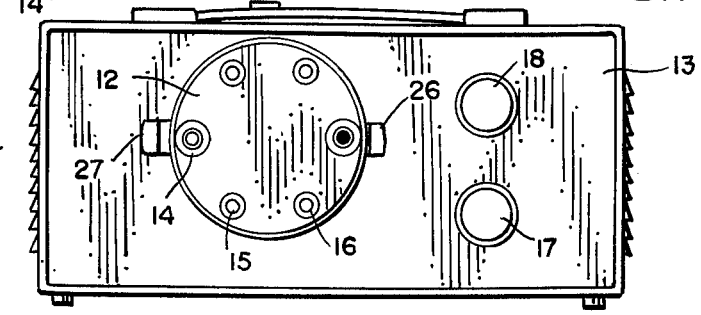

DOOR CLOSURE FOR FIBER OPTIC LIGHT SOURCE

Background

This invention relates to fiber optic light sources and finds particular utility in a fiber optic light source which includes a rotatably mounted bundle receptacle which is adapted to receive two or more fiber optic light bundles.

Fiber optic light sources are used to illuminate the ends of fiber optic light bundles which transmit light to fiber optic lighted instruments. One end of the fiber optic bundle is conventionally inserted into an opening in a bundle receptacle, and the opening is aligned with the light source. The light is transmitted through the bundle to the instrument at the other end of the bundle. Typical uses of fiber optic lighted instruments include medical examinations and surgery.

A physician or other user of fiber optic lighted instruments might wish to use two or more instruments at the same time, or he might wish to use instruments made by different manufacturers which have different types of receptacle ends. U.S. Pat. No. 3,638,013 describes a fiber optic light source which is provided with a receptacle or plug having three bundle-receiving openings. The receptacle is rotatable so that one, two, or all three of the openings are positioned to be illuminated by the light source. FIGS. 13–18 of this patent illustrate a receptacle in which the bundle-receiving openings are of different size so that different sizes of fiber optic bundles can be used.

U.S. Pat. No. 3,831,017 describes a rotatable selector turret for a fiber optic light source on which two pairs of receptacles are mounted. One of the pairs of receptacles are of the same size so that two instruments of the same manufacture can be used at the same time, and the other pair of receptacles are of different size so that two instruments of different manufacture can be used at the same time. The turret can be rotated to align the desired pair with the light source.

Fiber optic light sources which are capable of illuminating two or more fiber optic bundles at the same time are sometimes used with only a single bundle. At other times, although two bundles might be plugged into the receptacle of the light source, the user will wish to illuminate only one of the bundles. Accordingly, fiber optic light sources which include a pair of lamps for simultaneously illuminating a pair of bundles conventionally include a selector switch for turning either or both lamps on. However, at times it may be desirable to shut off light from one or both bundles without moving the lamp selector switch or rotating the bundle receptacle. Further, even if only one lamp is on, light from this lamp can shine through the illuminating opening provided for the other lamp. This "leakage" of light through the opening for the unlit lamp can be distracting and can be undesirable if the field surrounding the area in which the lighted fiber optic instrument is being used is to be kept dark.

SUMMARY

The invention provides a door closure for a fiber optic light source which permits light from the source to be shut off from one or more bundle receptacle openings without moving the lamp selector switch or rotating the receptacle. Each of the openings through which light is transmitted to the receptacle can be opened and closed by a door which is slidably mounted on the frame of the fiber optic light source, and the door is frictionally retained in the desired position. If only one bundle is to be illuminated, the door for a second of such bundles can be closed to prevent leakage of light through the receptacle openings for the second bundle.

DESCRIPTION OF THE DRAWINGS

The invention will be explained in conjunction with an illustrative embodiment shown in the accompanying drawing, in which FIG. 1 is a perspective view of a fiber optic light source equipped with light closure doors in accordance with the invention;

FIG. 2 is an exploded perspective view of the front portion of the fiber optic light source;

FIG. 3 is an enlarged fragmentary sectional view taken along the line 3—3 of FIG. 1; and FIG. 4 is a front elevational view of the fiber optic light source of FIG. 1.

DESCRIPTION OF SPECIFIC EMBODIMENT

Referring first to FIG. 1, the numeral 10 designates generally a fiber optic light source which includes an outer box-like frame 11 which houses a pair of projection lamps (not shown) for illuminating the ends of conventional fiber optic light bundles. A bundle receptable 12 is rotatably mounted on a front plate 13 of the frame, and the receptacle is provided with three pairs 14, 15, and 16 of diametrically opposed openings into which the ends of fiber optic light bundles can be inserted. A lamp selector switch for turning on either or both of the projection lamps is operated by a knob 17, and a rheostat for varying the intensity of the lamps is operated by a knob 18. Access to the lamp compartment is provided by a door 19 in the top of the frame, and the light source can be transported by a carrying handle 20.

Referring now to FIGS. 2 and 3, the frame plate 13 is provided with a pair of light openings 22 and 23, and each of the openings is aligned with one of the projection lamps. A third opening 24 is provided between the light openings for receiving a mounting pin 25 for the receptacle. The mounting pin 25 is rotatably received by the opening 24, and the receptacle may be rotated to selectively align any of the pairs 14–16 of openings therein with the light openings 22 and 23 in the frame plate. Each of the light openings can be opened or closed to permit light from the associated lamp to pass through or be blocked from the aligned openings in the receptacle by doors 26 and 27 which are slidably mounted in front of the frame plate by a circular mounting plate 28.

Each of the doors includes a generally rectangular closure portion 29 which is provided with a light opening 30, an operating handle 31, and an L-shaped connecting portion 32 which connects the handle to the closure portion. The closure portion 29 is wider than the connecting portion and includes a pair of converging shoulders 33.

The mounting plate 28 is provided with a central opening 35 through which the mounting pin 25 extends and a pair of radially outwardly extending slots 36 and 37 in which the doors 26 and 27, respectively, are slidably positioned. The maximum width of the slots 36 and 37 corresponds to the width of the closure portions 29 of the doors, and each slot includes a narrowed mouth portion 38 which cooperates with the converging shoulders 33 of the closure portion to prevent withdrawal of the closure portion from the slot.

A generally cylindrical Teflon bushing 40 is snugly received in each of the light openings 22 and 23 in the frame plate and includes an annular flange 41 which extends radially outwardly over the front surface of the frame plate. The outer diameter of the flange is less than the width of the slots 36 and 37 in the mounting plate, and the mounting plate is secured to the frame plate with the flanges of the bushings positioned within the slots. The mounting plate is secured to the frame plate by screws 42 which extend through openings 43 in the frame plate.

The mounting pin 25 includes a head portion 25a and a shaft portion 25b which is secured within a center opening 44 in the receptacle, as by a jam fit, adhesive, or the like. The diameter of the head 25a of the mounting pin is slightly less than the diameter of the openings 24 and 35 in the frame plate and mounting plate, respectively, and the head is prevented from passing through the openings by a snap ring 45 which is positioned within a groove 46 in the head.

Rotation of the receptacle is facilitated by a washer 47 which is positioned between the receptacle and the mounting plate and a washer 48 which is positioned between the snap ring and the frame plate. The washers are advantageously made of material which is slightly compressible, such as Teflon, and the receptacle is held snugly against the washer 47 by locating the snap ring in groove 46 so that the washers 47 and 48 must be compressed slightly before the snap ring can be inserted.

The thickness of the closure portions 29 of the doors 26 and 27 corresponds generally to the thickness of the mounting plate 28, and the thickness of the flanges 41 of the bushings 40 corresponds generally to the thickness of the washer 47. The receptacle therefore presses each of the doors against its associated bushing, providing a frictional force on each door which restrains sliding movement of the door in the slot of the mounting plate and frictionally retains the door in any selected position within the slot.

A pair of detent balls 50 (FIG. 3) are carried by the receptacle within bores 51, and the balls are biased rearwardly against the mounting plate by coil springs 52. The mounting plate is provided with a detent recess 53 for each of the openings of the receptacle, and as each pair of openings becomes aligned with the light openings 22 and 23 of the frame plate as the receptacle is rotated, the two detent balls register with two of the detent recesses and maintain the receptacle in the desired position.

In the particular embodiment illustrated, each of the openings of a particular pair of openings in the receptacle is of the same size and is adapted to receive a fiber optic light bundle of the same manufacture so that two instruments of the same manufacture can be used at the same time. Each of the pairs 14–16 are of different size, however, so that instruments of three different manufacture can be used by aligning the appropriate pair of openings with the light openings. If desired, however, the openings of each pair can be sized to receive light bundles of different manufacture so that two instruments of different manufacture can be used simultaneously.

When the doors 26 and 27 are pushed inwardly within the slots of the mounting plate, i.e., toward the center of the mounting plate, so that the inner edges of the doors engage the inner edges of the slots, the openings in the doors are positioned inwardly of the light openings 22 and 23 of the frame plate. In this closed position, occupied by the right door 26 in FIGS. 3 and 4, an imperforate portion of the closure portion of the door covers the light opening. The doors are pressed against the bushing 40 by the receptacle 12, and light from both of the lamps is blocked from passing through the light opening and into the aligned opening of the receptacle.

When a door is pulled outwardly until the detent shoulders 33 thereof engage the detent stops 38 of the mounting plate, the opening in the door is aligned with the light opening in the frame plate. This open position of the door is occupied by the left door 27 in FIGS. 3 and 4. Light can pass through the light opening 23 of the frame plate, through the opening in the door, and into the aligned opening 14 in the receptacle. However, the engagement of the door with the bushing 40 prevents leakage of light laterally outwardly from between the door and the frame plate.

If a light bundle is plugged into both of the receptacle openings 14 in FIG. 3, the bundle on the left will be illuminated by the lamp behind the light opening 23. However, the bundle on the right will not be illuminated since the right door is in the closed position. When it is desired to illuminate the right bundle, the right door 26 need only be pulled outwardly to the opened position.

If a bundle is not plugged into the right opening 14 in FIG. 3, the door 26 will prevent light from shining through the receptacle opening. It will be appreciated that the projector lamps used in fiber optic light sources provide intense light which should not be viewed directly, and the doors provide a safeguard against this possibility.

Even if the lamp behind the light opening 22 is turned off, light from the other lamp can shine through the light opening 22 and through the aligned opening 14 in the receptacle if the door is not closed. Although this light is not as intense as light which shines directly through the opening 22 from the associated lamp, the light can be undesirable. However, when the door 26 is in the closed position as illustrated in FIG. 3, such leakage of light is prevented.

The doors illustrated are provided with openings which are aligned with the openings in the frame plate and the receptacle when the doors are in the open position. However, the doors can be solid, and each door can be moved to an open position by withdrawing the door until the inner edge thereof is positioned outwardly of the aligned openings in the frame plate and receptacle.

While in the foregoing specification a detailed description of a specific embodiment of the invention was set forth for the purpose of illustration, it is to be understood that many of the details herein given may be varied considerably by those skilled in the art without departing from the spirit and scope of the invention.

We claim:

1. In a fiber optic light source for illuminating a fiber optic bundle, the light source including a frame, illumination means within the frame for providing light, the frame being provided with a pair of openings through which light from the illumination means can pass, and a receptacle for a fiber optic light bundle rotatably mounted on the frame and having a plurality of pairs of openings, each pair of openings being alignable with the openings in the frame, the improvement comprising a pair of doors movably mounted between the frame and the receptacle, each of the doors being movable between a first position in which the door covers one of the openings in the frame and light from the illumination means is blocked from passing into the aligned opening in the receptacle and a second position in which an opening in the frame is not covered by the door and light can pass through an opening in the frame into the aligned opening in the receptacle, each of the doors being frictionally retained in its first and second positions by the receptacle without requiring removal of said fibre optic light bundle when each of said doors is in said first position.

2. The structure of claim 1 including means for mounting the receptacle on the frame and for urging the receptacle against the doors.

3. The structure of claim 1 including a door mounting plate between the receptacle and the frame, the door mounting plate having a pair of slots in which the doors move between their first and second positions.

4. The structure of claim 3 in which each of the doors and the mounting plate include cooperating detent means for preventing movement of each door beyond its first or second position.

5. The structure of claim 4 in which each of the slots has a narrowed mouth portion which is engageable with shoulders on the associated door, the narrowed mouth portion and the shoulders providing the cooperating detent means.

6. The structure of claim 1 including a bushing mounted within each of the openings in the frame, each door being frictionally retained in its first and second positions between the receptacle and the bushing of the associated opening in the frame.

7. The structure of claim 6 including means for mounting the receptacle on the frame and for urging the receptacle toward the doors and the bushings whereby each of the doors is clamped between the receptacle and one of the bushings.

* * * * *